United States Patent
Gutiérrez Rodríguez et al.

(10) Patent No.: US 10,526,276 B2
(45) Date of Patent: Jan. 7, 2020

(54) DREAM NEURONAL CALCIUM SENSOR-MODULATING COMPOUNDS, AND THERAPEUTIC USES THEREOF

(71) Applicants: CONSEJO SUPERIOR DE INVESTIGACIONES CIENTÍFICAS, Madrid (ES);
(Continued)

(72) Inventors: Marta Gutiérrez Rodríguez, Madrid (ES); Pilar Cercos Pita, Madrid (ES); María Rosario Herranz Herranz, Madrid (ES); María Teresa García López, Madrid (ES);
(Continued)

(73) Assignees: CONSEJO SUPERIOR DE INVESTIGACIONES CIENTÍFICAS, Madrid (ES); CENTRO DE INVESTIGACIÓN BIOMÉDICA EN RED DE ENFERMEDADES NEURODEGENERATIVAS (CIBERNED), Madrid (ES); UNIVERSIDAD AUTÓNOMA DE MADRID, Madrid (ES)

( * ) Notice: Subject to any disclaimer, the term of this patent is extended or adjusted under 35 U.S.C. 154(b) by 95 days.

(21) Appl. No.: 15/538,341

(22) PCT Filed: Dec. 17, 2015

(86) PCT No.: PCT/ES2015/070923
§ 371 (c)(1),
(2) Date: Jun. 21, 2017

(87) PCT Pub. No.: WO2016/102727
PCT Pub. Date: Jun. 30, 2016

(65) Prior Publication Data
US 2018/0037538 A1  Feb. 8, 2018

(30) Foreign Application Priority Data
Dec. 22, 2014  (ES) .................................. 201431898

(51) Int. Cl.
*C07C 233/33*  (2006.01)
*C07D 233/64*  (2006.01)
(Continued)

(52) U.S. Cl.
CPC .......... *C07C 233/33* (2013.01); *C07C 233/31* (2013.01); *C07C 233/55* (2013.01);
(Continued)

(58) Field of Classification Search
None
See application file for complete search history.

(56) References Cited

U.S. PATENT DOCUMENTS

2006/0135620 A1    6/2006  Mintz et al.
2009/0240052 A1*   9/2009  Yokotani ............... C07C 233/51
                                                          544/124
2011/0294853 A1   12/2011  Pelcman et al.

FOREIGN PATENT DOCUMENTS

EP           1876169      1/2008
WO    WO2004/022525 A1    3/2004
(Continued)

OTHER PUBLICATIONS

Isomer. (1992). In C. G. Morris (Ed.), Academic Press Dictionary of Science and Technology (4th ed.). Oxford, UK: Elsevier Science & Technology. Retrieved from https://search.credoreference.com/content/entry/apdst/isomer/0?institutionId=743 (Year: 1992).*
(Continued)

*Primary Examiner* — Amy C Bonaparte
(74) *Attorney, Agent, or Firm* — Womble Bond Dickinson (US) LLP

(57) ABSTRACT

The present invention relates to a group of compounds with a structural nucleus derived from phenylacetamide, having the following formula (I):
(Continued)

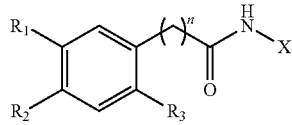

(I)

that can modulate the DREAM neuronal calcium sensor. Consequently, the present invention also relates to the use of these compounds for the treatment or prevention of disorders or diseases in which DREAM levels are above or below physiologically normal levels.

6 Claims, 2 Drawing Sheets

(71) Applicants: CENTRO DE INVESTIGACIÓN BIOMÉDICA EN RED DE ENFERMEDADES NEURODEGENERATIVAS (CIBERNED), Madrid (ES); UNIVERSIDAD AUTÓNOMA DE MADRID, Madrid (ES)

(72) Inventors: María Carmen Valenzuela Miranda, Madrid (ES); José Ramón Naranjo Orovio, Madrid (ES); Britt Mellstrom, Madrid (ES); Paz González Pérez, Madrid (ES); María Mercedes Martín Martínez, Madrid (ES); José Manuel Dopazo Santos, Madrid (ES)

(51) Int. Cl.
    *C07C 233/31*      (2006.01)
    *C07C 233/55*      (2006.01)
    *C07C 235/38*      (2006.01)
    *C07C 237/42*      (2006.01)

(52) U.S. Cl.
    CPC .......... *C07C 235/38* (2013.01); *C07C 237/42* (2013.01); *C07D 233/64* (2013.01)

(56) References Cited

FOREIGN PATENT DOCUMENTS

| WO | WO-2005016870 | 2/2005 |
| WO | WO-2005016879 | 2/2005 |
| WO | WO-2012059442 | 5/2012 |
| WO | WO-2012095548 | 7/2012 |
| WO | WO-2012119978 | 9/2012 |
| WO | WO-2013030358 | 3/2013 |

OTHER PUBLICATIONS

Suthar ("New Organic Polymers, II" Die Angewandte Makromolekulare Chemie, 93, 1981, p. 199-209) (Year: 1981).*
Glunz ("Reduction of Sterically Hindered a,a-disubstituted Amino Esters" Synthetic Communications, 29, 1999, p. 835-842) (Year: 1999).*
Greene "N-Triphenylmethylamine" Protective Groups in Organic Synthesis, 3rd ed, 1999, p. 583-584 (Year: 1999).*
Mehta ("Benzoquinazolines. II. Synthesis of 2-phenyl- and 2-benzyl-4-oxobenzoquinazolines and spectra studies on them" Indian Journal of Chemistry, 6, 1968, p. 294-296) (Year: 1968).*
Carrion, et al., "DREAM is a Ca2+-regulated transcriptional repressor", Letters to Nature, Nature, vol. 398, Mar. 4, 1999, 80-84.
Rivas, et al., "The DREAM Protein Is Associated with Thyroid Enlargement and Nodular Development", Mol Endocrinol, vol. 23, No. 6, Jun. 2009, 862-870.
International Search Report dated Sep. 2, 2016, for PCT application No. PCT/ES2015/070923.
Written Opinion of the International Searching Authority dated Sep. 2, 2016, for PCT application No. PCT/ES2015/070923.
Extended European Search Report, dated Jul. 18, 2018, for European application No. 15872009.4.
Mehta, et al., "Benzoquinazolines: Part II-Synthesis of 2-phenyl-& 2-benzyl-4-keto-benzoquinazolines & their spectral studies", Indian Journal of Chemistry, vol. 6, Jun. 1968, pp. 294-296.
Peifer, et al., "Implications for selectivity of 3,4-diarylquinolinones as p38.alpha.MAP kinase inhibitors", & "Supporting Information", Bioorganic & Medicinal Chemistry Letters, vol. 18, No. 4, Jan. 5, 2008, pp. 1431-1435.
Kreimeyer, et al., "Evaluation and Biological Properties of Reactive Ligands for the Mapping of the Glycine Site on the N-methyl-D-aspartate (NMDA) Receptor", Journal of Medicinal Chemistry, vol. 42, No. 2, Oct. 5, 1999, pp. 4394-4404.

* cited by examiner

DREAM NEURONAL CALCIUM SENSOR-MODULATING COMPOUNDS, AND THERAPEUTIC USES THEREOF

CROSS-REFERENCE TO RELATED APPLICATIONS

The present patent application is a national phase application of International Application No. PCT/ES2015/070923, filed Dec. 17, 2015, which claims priority to Spanish Application No. P201431898, filed Dec. 22, 2014, the disclosures of which are incorporated herein by reference.

The present invention relates to a group of compounds with a structural nucleus derived from phenylacetamide, the compounds of which can modulate the DREAM neuronal calcium sensor, whereby these compounds are useful for the treatment or prevention of disorders or diseases in which DREAM expression levels are deregulated.

STATE OF THE ART

The DREAM (Downstream Regulatory Element Antagonist Modulator) protein, also known as potassium channel interacting calsenilin or protein 3 (KCHIP-3), is a multifunctional calcium-binding protein belonging to the large family of proteins with EF hand domains and shares a high sequence homology with other members of the subfamily of Neuronal Calcium Sensors (NCS). DREAM controls the expression levels and/or the activity of different proteins related to calcium homeostasis, neuron excitability and neuronal survival (Carrion, A. m. et al Nature 1999, 398, 80). Thus, DREAM is involved in the regulation of gene expression, apoptosis, modulation of potassium channels kV4 and of L- and T-type calcium channels, and in the modulation of the NMDA and thyrotropin receptor (TSHR) (Rivas, M. et al. *Mol Endocrinol.* 2009, 23, 862). Moreover, recently it has been described that DREAM has a key role in the dopaminergic system. Various in vitro and in vivo studies have concluded that DREAM is involved in the regulation of the processes of apoptosis and accumulation of amyloid-β peptide, in the processing of N-cadherin through interaction with presenilin, in regulating levels of dyskinesia induced by L-3,4-dihydroxyphenylalanine (L-DOPA) and the suppression of inflammatory signal mediated by the NF-kB transcription factor.

Taking into account the processes in which the DREAM protein is involved, it would be useful to have modulating compounds of this protein for the treatment of diseases in which DREAM has an alteration in their expression levels, such as for example in neurodegenerative diseases, chronic pain and inflammation processes. Document WO2012/095548 describes a series of DREAM protein modulators for the treatment of neurodegenerative diseases such as Alzheimer's disease or Huntington's disease.

Document WO2013/030358 describes a series of compounds derived from 4-naphthalene-2-carboxylic acids and the use thereof for treating diseases such as Alzheimer's, Down syndrome, Huntington's, schizophrenia or depression.

Document WO2005/016870 describes a series of compounds derived from benzoic acid substituted by an amide group, HM74A receptor activators, although this receptor is related to lipid metabolism.

Document WO2012/059442 describes an amide group of acylaminophthalic acid, which are inhibitors of neurotrypsin and are useful for treating diseases such as schizophrenia or Alzheimer's disease.

DESCRIPTION OF THE INVENTION

The inventors have found a family of compounds that can modulate the activity of the DREAM protein, so they are useful for treating diseases in which the control of the levels of this protein is required to reduce or eliminate symptoms.

Therefore, in a first aspect, the present invention relates to the compound of formula (I):

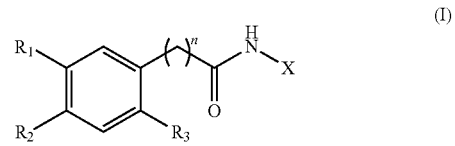

(I)

or any of its pharmaceutically acceptable salts, solvates or isomers where $R_1$ is selected from H, halogen or OR', R' being selected from H or optionally substituted aryl, $R_2$ is selected from H, halogen or OH,
$R_3$ is selected from H or halogen,
n is selected from 1 or 2,
X is selected from the following groups:

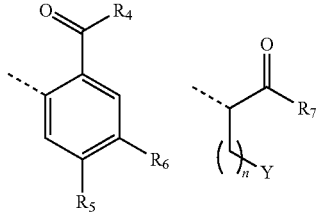

wherein
$R_4$ is selected from OH, aryl, —$(CH_2)_m$-aryl, m being a value selected from 1 to 3, OR" or NHR", R" being selected from aryl or $C_1$-$C_4$ alkyl,
$R_5$ is selected from H, halogen, OR', optionally substituted aryl or $C_2$-$C_4$ alkynyl,
$R_6$ is selected from H, or optionally substituted aryl,
or $R_5$ and $R_6$ form, together with phenyl to which are joined a naphthalene group, $R_7$ is an OR" group and
Y is selected from optionally substituted aryl or optionally substituted heteroaryl,
provided that the compound of formula (I) is not one of the following compounds:
4-chloro-2-(2-(3,4-dichlorophenyl) acetamide) benzoic acid (5),
3-(2-(3,4-dichlorophenyl) acetamide)-2-naphthoic acid (20), The term "alkyl", in the present invention, refers to radicals of hydrocarbon, linear or branched chains having 1 to 6 carbon atoms, preferably 1 to 4, and which bind to the rest of the molecule by a single bond, for example, methyl, ethyl, n-propyl, i-propyl, n-butyl, tert-butyl, sec-butyl, n-pentyl, n-hexyl etc. Alkyl groups may be optionally substituted by one or more substituents such as halogen (referred to as haloalkyl), hydroxyl, alkoxy, carboxyl, carbonyl, cyano, acyl, alkoxycarbonyl, amino, nitro, mercapto and alkylthio.

The term "aryl" in the present invention relates to a phenyl, naphthyl, indenyl, phenanthryl or anthracyl radical. The aryl radical may be optionally substituted by one or more substituents such as alkyl, haloalkyl, aminoalkyl, dialkylamino, hydroxyl, alkoxy, phenyl, mercapto, halogen, nitro, cyano and alkoxycarbonyl.

The term "heteroaryl" refers to an aryl having at least one heteroatom selected from S, N or O. The heteroaryl radical may be optionally substituted by at least one of its carbon atoms or heteroatoms by one or more substituents such as alkyl, haloalkyl, aminoalkyl, dialkylamino, hydroxyl, alkoxy, phenyl, mercapto, halogen, nitro, cyano and alkoxycarbonyl.

The term "alkynyl" refers to radicals of linear or branched hydrocarbon chains having 2 to 6 carbon atoms, preferably 2 to 4 and containing one or more carbon-carbon triple bonds, for example, ethyne, propyne, etc. Alkynyl radicals may be optionally substituted by one or substituents such as alkyl, haloalkyl, aminoalkyl, dialkylamino, hydroxyl, alkoxy, phenyl, mercapto, halogen, nitro, cyano and alkoxycarbonyl.

The term "halogen" refers to fluorine, chlorine bromine or iodine.

In a preferred embodiment, $R_1$ is halogen and more preferably chlorine.

In another preferred embodiment, $R_1$ is an OR' group, R' being selected from H or phenyl.

In another preferred embodiment, $R_1$ is H.

In another preferred embodiment, $R_2$ is halogen and more preferably chlorine.

In another preferred embodiment, R 2 is H.

In another preferred embodiment, $R_2$ is OH.

In another preferred embodiment, $R_3$ is H.

In another preferred embodiment, $R_3$ is halogen and more preferably fluorine.

In another preferred embodiment, X is the following group:

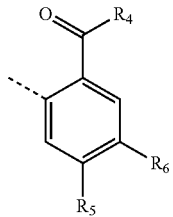

In a preferred embodiment, $R_4$ is OH.

In another preferred embodiment, $R_4$ is a NHR" group.

In another preferred embodiment, $R_4$ is an OR" group.

In a more preferred embodiment, R" is methyl.

In another preferred embodiment, $R_4$ is a phenyl.

In another preferred embodiment, $R_5$ is halogen and more preferably chlorine or bromine.

In another preferred embodiment, $R_5$ is an OR" group, R" being $C_1$-$C_4$ alkyl and more preferably, R" is methyl.

In another preferred embodiment, $R_5$ is H.

In another preferred embodiment, $R_5$ is an optionally substituted phenyl and $R_6$ is H.

In a more preferred embodiment, $R_5$ is a phenyl substituted by a $C_1$-$C_4$ alkyl. In an even more preferred embodiment, $R_5$ is selected from 2-methylphenyl, 4-n-butylphenyl or 4-tert-butylphenyl.

In another preferred embodiment, $R_5$ is a $C_2$-$C_4$ alkyl and more preferably ethynyl.

In another preferred embodiment, $R_6$ is an optionally substituted phenyl and $R_5$ is H. In a more preferred embodiment, $R_6$ is a phenyl substituted by a $C_1$-$C_4$ alkyl. In an even more preferred embodiment, $R_6$ is selected from 2-methylphenyl, 4-n-butylphenyl or 4-tert-butylphenyl.

In another preferred embodiment, $R_5$ and $R_6$ form together with the phenyl to which are joined a naphthalene group.

In another preferred embodiment, the compound of formula (I) described above is selected from the following list:

2-[2-(3,4-dichlorophenyl)acetylamino]-4-methoxybenzoic acid, (7)

4-chloro-2-[2-(3-phenoxyphenyl)acetylamino] benzoic acid (9), 4-chloro-2-[2-(4-chloro-2-fluorophenyl)acetylamino] benzoic acid, (10)

4-chloro-2-[2-(3,4-dichlorophenyl)acetylamino] methyl benzoate, (13)

4-chloro-2-[2-(3,4-dihydroxyphenyl)acetylamino] benzoic acid, (15)

4-chloro-2-[3-(3,4-dichlorophenyl)propanoylamino] benzoic acid, (16)

4-chloro-2-[2-(3,4-dichlorophenyl)acetylamino]-N-methylbenzamide, (21)

3-[2-(3-phenoxyphenyl)acetylamino]-2-naphthoic acid, (22)

3-[3-(3-(3,4-dichlorophenyl)propanoylamino)]-2-naphthoic acid, (23)

4-bromo-2-[2-(3,4-diclorophenyl)acetylamino] benzoic acid, (32)

2-[2-(3,4-dichlorophenyl)acetylamino]-5-(4'-n-butylphenyl) benzoic acid, (34)

2-[2-(3,4-dichlorophenyl)acetylamino]-4-(4'-n-butylphenyl) benzoic acid, (35)

2-[2-(3,4-dichlorophenyl)acetylamino]-5-(4'-tert-butylphenyl) benzoic acid, (36)

2-[2-(3,4-dichlorophenyl)acetylamino]-5-(2'-methylphenyl) benzoic acid, (37)

2-[3-(3,4-dichlorophenyl)propanoylamino]-5-(4'-n-butylphenyl) benzoic acid, (38)

2-[2-(3,4-dichlorophenyl)acetylamino]-4-phenylbenzoic acid, (39)

2-[2-(3,4-dichlorophenyl)acetylamino]-4-(2'-methylphenyl) benzoic acid, (40)

2-[3-(3,4-dichlorophenyl)propanoylamino]-4-phenylbenzoic acid, (41)

2-[2-(3,4-dichlorophenyl)acetylamino]-5-phenylbenzoic acid, (42)

2-[3-(3,4-dichlorophenyl)propanoylamino]-5-(4'-tert-butylphenyl) benzoic acid, (43)

2-[3-(3,4-dichlorophenyl)propanoylamino]-5-(2'-methylphenyl) benzoic acid, (44)

2-[3-(3,4-dichlorophenyl)propanoylamino]-4-(2'-methylphenyl) benzoic acid, (45)

2-[2-(3,4-dichlorophenyl)acetylamino]-4-ethynylbenzoic acid, (46)

2-[2-(3,4-dichlorophenyl)acetylamino]-methyl 5-phenylbenzoate, (48)

2-[2-(3,4-dichlorophenyl)acetylamino]-5-(2'-methylphenyl) methyl benzoate, (49)

2-[2-(3,4-dichlorophenyl)acetylamino]-5-(4'-tert-butylphenyl) methyl benzoate, (50)

2-[2-(3,4-dichlorophenyl)acetylamino]-5-(4'-n-butylphenyl) methyl benzoate, (51)

2-[2-(3,4-dichlorophenyl)acetylamino]-methyl 4-phenylbenzoate, (52)

2-[2-(3,4-dichlorophenyl)acetylamino]-4-(2'-methylphenyl) methyl benzoate, (53)

2-[2-(3,4-dichlorophenyl)acetylamino]-4-(4'-n-butylphenyl) methyl benzoate, (54)

2-[3-(3,4-dichlorophenyl)propanoylamino]-methyl 5-phenylbenzoate, (55)

2-[3-(3,4-dichlorophenyl)propanoylamino]-5-(2'-methylphenyl) methyl benzoate, (56)

2-[3-(3,4-dichlorophenyl)propanoylamino]-5-(4'-n-butylphenyl) methyl benzoate, (57)

2-[3-(3,4-dichlorophenyl)propanoylamino]-methyl 4-phenylbenzoate, (58)

2-[3-(3,4-dichlorophenyl)propanoylamino]-4-(2'-methylphenyl) methyl benzoate, (59)

2-[3-(3,4-dichlorophenyl)propanoylamino]-4-(4'-n-butylphenyl) methyl benzoate, (60)

2-[3-(3,4-dichlorophenyl)propanoylamino]-5-phenylbenzoic acid, (61)

N-(2-benzoylphenyl)-2-(3,4-dichlorophenyl)acetamide (63) and

2-[3-(3,4-dichlorophenyl)propanoylamino]-4-(4'-n-butylphenyl) benzoic acid, (64).

In a preferred embodiment, Y is a phenyl optionally substituted by OH, $C_1$-$C_4$ alkyl or halogen, and more preferably phenyl is substituted by at least one OH in any of the positions thereof.

In another preferred embodiment, Y is a heteroaryl that is selected from among indole or imidazol optionally substituted by an OH, $C_1$-$C_4$ alkyl or halogen.

In a more preferred embodiment, X is the following group:

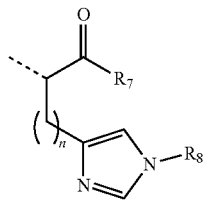

wherein $R_8$ is an optionally substituted $C_1$-$C_4$ alkyl,

In an even more preferred embodiment, $R_7$ is an OR" group, R" being methyl.

In another even more preferred embodiment, $R_8$ is a $C_1$-$C_4$ alkyl substituted by at least one phenyl.

In another more preferred embodiment, the compound (I) is (2R)-2-[2-(3,4-dichlorophenyl)acetylamino]-3-(1-trityl-1H-imidazol-4-yl) methyl propanoate (62).

The compounds of the present invention represented by formula (I), and more specifically, the specific compounds belonging to this general formula described above, may include isomers depending on the presence of multiple bonds (for example, Z, E), including optical isomers or enantiomers, depending on the presence of chiral centres. The individual isomers, enantiomers or diastereoisomers and the mixtures thereof fall within the scope of the present invention. The individual enantiomers or diastereoisomers, as well as the mixtures thereof, may be separated using conventional techniques.

The compounds of the invention may be in crystalline form as free compounds or as solvates and it is intended to include both forms within the scope of the present invention. In this regard, the term "solvate", as used herein, includes both pharmaceutically acceptable solvates, i.e. solvates of the compound of formula (I) that may be used in the preparation of a medicinal product, and pharmaceutically unacceptable solvates, which can be useful in the preparation of solvates or pharmaceutically acceptable salts. The nature of the pharmaceutically acceptable solvate is not critical provided it is pharmaceutically acceptable. In a particular embodiment, the solvate is a hydrate. Solvates may be obtained by conventional methods of solvation that are well known by those skilled in the art.

Another aspect of the invention relates to a pharmaceutical composition comprising a compound of formula (I) as described above.

Another aspect of the invention relates to the use of a compound of formula (I):

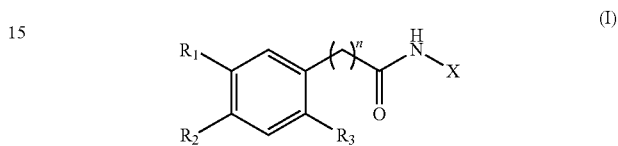

or any of the pharmaceutically acceptable salts, solvates or isomers thereof, wherein $R_1$, $R_2$, $R_3$, n and X are defined as above, for the manufacture of a medicinal product.

In another preferred embodiment, the compound of formula (I) is selected from the following list:

4-chloro-2-[2-(3,4-dichlorophenyl)acetylamino) benzoic acid (5),

2-[2-(3,4-dichlorophenyl)acetylamino]-4-methoxybenzoic acid, (7)

4-chloro-2-[2-(3-phenoxyphenyl)acetylamino] benzoic acid (9), 4-chloro-2-[2-(4-chloro-2-fluorophenyl)acetylamino] benzoic acid, (10)

4-chloro-2-[2-(3,4-dichlorophenyl)acetylamino] methyl benzoate, (13)

4-chloro-2-[2-(3,4-dihydroxyphenyl)acetylamino] benzoic acid, (15)

4-chloro-2-[3-(3,4-dichlorophenyl)propanoylamino] benzoic acid, (16)

3-[2-(3,4-dichlorophenyl)acetylamino)-2-naphthoic acid (20), 4-chloro-2-[2-(3,4-dichlorophenyl)acetylamino]-N-methylbenzamide, (21)

3-[2-(3-phenoxyphenyl)acetylamino]-2-naphthoic acid, (22)

3-[3-(3-(3,4-dichlorophenyl)propanoylamino)]-2-naphthoic acid, (23)

4-bromo-2-[2-(3,4-diclorophenyl)acetylamino] benzoic acid, (32)

2-[2-(3,4-dichlorophenyl)acetylamino]-5-(4'-n-butylphenyl) benzoic acid, (34)

2-[2-(3,4-dichlorophenyl)acetylamino]-4-(4'-n-butylphenyl) benzoic acid, (35)

2-[2-(3,4-dichlorophenyl)acetylamino]-5-(4'-tert-butylphenyl) benzoic acid, (36)

2-[2-(3,4-dichlorophenyl)acetylamino]-5-(2'-methylphenyl) benzoic acid, (37)

2-[3-(3,4-dichlorophenyl)propanoylamino]-5-(4'-n-butylphenyl)benzoic acid, (38)

2-[2-(3,4-dichlorophenyl)acetylamino]-4-phenylbenzoic acid, (39)

2-[2-(3,4-dichlorophenyl)acetylamino]-4-(2'-methylphenyl) benzoic acid, (40)

2-[3-(3,4-dichlorophenyl)propanoylamino]-4-phenylbenzoic acid, (41)

2-[2-(3,4-dichlorophenyl)acetylamino]-5-phenylbenzoic acid, (42)

2-[3-(3,4-dichlorophenyl)propanoylamino]-5-(4'-tert-butyl-phenyl)benzoic acid, (43)
2-[3-(3,4-dichlorophenyl)propanoylamino]-5-(2'-methyl-phenyl)benzoic acid, (44)
2-[3-(3,4-dichlorophenyl)propanoylamino]-4-(2'-methyl-phenyl)benzoic acid, (45)
2-[2-(3,4-dichlorophenyl)acetylamino]-4-ethynylbenzoic acid, (46)
2-[2-(3,4-dichlorophenyl)acetylamino]-methyl 5-phenyl-benzoate, (48)
2-[2-(3,4-dichlorophenyl)acetylamino]-5-(2'-methylphenyl) methyl benzoate, (49)
2-[2-(3,4-dichlorophenyl)acetylamino]-5-(4'-tert-butylphe-nyl)methyl benzoate, (50)
2-[2-(3,4-dichlorophenyl)acetylamino]-5-(4'-n-butylphenyl) methyl benzoate, (51)
2-[2-(3,4-dichlorophenyl)acetylamino]-methyl 4-phenyl-benzoate, (52)
2-[2-(3,4-dichlorophenyl)acetylamino]-4-(2'-methylphenyl) methyl benzoate, (53)
2-[2-(3,4-dichlorophenyl)acetylamino]-4-(4'-n-butylphenyl) methyl benzoate, (54)
2-[3-(3,4-dichlorophenyl)propanoylamino]-methyl 5-phe-nylbenzoate, (55)
2-[3-(3,4-dichlorophenyl)propanoylamino]-5-(2'-methyl-phenyl)methyl benzoate, (56)
2-[3-(3,4-dichlorophenyl)propanoylamino]-5-(4'-n-butyl-phenyl)methyl benzoate, (57)
2-[3-(3,4-dichlorophenyl)propanoylamino]-methyl 4-phe-nylbenzoate, (58)
2-[3-(3,4-dichlorophenyl)propanoylamino]-4-(2'-methyl-phenyl)methyl benzoate, (59)
2-[3-(3,4-dichlorophenyl)propanoylamino]-4-(4'-n-butyl-phenyl)methyl benzoate, (60)
2-[3-(3,4-dichlorophenyl)propanoylamino]-5-phenylben-zoic acid, (61)
(2R)-2-[2-(3,4-dichlorophenyl)acetylamino]-3-(1-trityl-1H-imidazol-4-yl) methyl propanoate (62)
N-(2-benzoylphenyl)-2-(3,4-dichlorophenyl)acetamide (63) and
2-[3-(3,4-dichlorophenyl)propanoylamino]-4-(4'-n-butyl-phenyl)benzoic acid, (64).

Another aspect of the invention relates to the use of a compound of formula (I) as described above to manufacture a medicinal product for treating a disease or disorder in which the DREAM protein has altered expression levels.

In the present invention, the expression "expression levels of the DREAM protein are altered" refers to the fact that in target tissue or cell, object of the treatment, the amount of DREAM protein in said target tissue or cell is above or below physiologically normal levels; the expression of the DREAM protein can be measured using techniques widely known by those skilled in the art, and therefore the measurement can refer to both the levels of protein and messenger RNA. This abnormal DREAM level affects signalling pathways in which this protein is involved, leading to different malfunctions that result in symptoms associated with various diseases. The compounds of formula (I) of the present invention are capable of modulating the function of DREAM such that abnormal levels of DREAM do not affect signalling pathways.

In a preferred embodiment, the disease or disorder in which expression levels of the DREAM protein are altered is selected from neurodegenerative disorders, cognitive disorders, sensory perception disorders, inflammatory response disorders and auto inflammatory diseases.

In a more preferred embodiment, the disease or disorder in which expression levels of the DREAM protein are altered is selected from Alzheimer's disease and other types of dementia, schizophrenia, Huntington's disease, dyskinesia, depression, disorders linked to Down's syndrome, chronic pain, neuropathic pain, allodynia, atherosclerosis, type-2 diabetes, rheumatoid arthritis, gout or acute respiratory distress syndrome.

For its therapeutic application, the compounds of the formula (I), the isomers, salts or solvates thereof, will preferably be in a pharmaceutically acceptable or substantially pure form, that is, having a pharmaceutically acceptable grade of purity, excluding the usual pharmaceutical additives such as diluents and carriers and not including material considered toxic at normal dosage levels. The levels of purity for the active ingredient are preferably greater than 50%, more preferably, greater than 70%, more preferably, greater than 90%. In a preferred embodiment, they are greater than 95% of the compound of formula (I) or of the salts, solvates or isomers thereof.

Unless stated otherwise, the compounds of the invention also include compounds that only differ in the presence of one or more isotopically enriched atoms. For example, compounds having said structure, except for the substitution of a hydrogen by a deuterium or tritium, or the substitution of a carbon by a carbon enriched in $^{13}C$ or $^{14}C$ or a nitrogen enriched in $^{15}N$, are within the scope of this invention.

The compounds of formula (I) for therapeutic use are prepared in solid form or in aqueous suspension, in a pharmaceutically acceptable diluent. These preparations may be administered by any suitable route of administration, for which reason said preparation is formulated in the dosage form suitable for the chosen route of administration. In a particular embodiment, the administration of the compound of formula (I), which is provided by this invention, is carried out by oral, topical, rectal or parenteral (including subcutaneous, intraperitoneal, intradermal, intramuscular, intravenous, etc.) route. A review of the different pharmaceutical forms of administration of drugs and excipients necessary for obtaining the same can be found, for example, in the "Tratado de Farmacia Galénica", (Treaty of Galenic Pharmacy), C. Faulí i Trillo, 1993, Luzán 5, S.A. Ediciones, Madrid, or in others that are common or similar to the Spanish and American Pharmacopeia.

The compounds described in the present invention, the pharmaceutically acceptable salts, isomers and/or solvates thereof, as well as the pharmaceutical compositions they contain may be used together with additional drugs to provide a combination therapy. Said additional drugs may form part of the same pharmaceutical composition or, alternatively, may be provided in the form of a separate composition for the simultaneous or non-simultaneous administration to that of the pharmaceutical composition comprising a compound of formula (I) or an isomer, solvate or pharmaceutically acceptable salt thereof.

Another aspect of the invention relates to a method of treating a disease or disorder in which expression levels of the DREAM protein are altered comprising the administration of a therapeutically effective amount of a compound of formula (I) as described above.

As used herein, the term "therapeutically effective amount" refers to the amount of the agent or compound capable of developing specific therapeutic action by their pharmacological properties, calculated to produce the desired effect and, in general, will be determined, among other causes, by the characteristics of the compounds as well as the age, condition of the patient, the severity of the alteration or disorder, and the route and frequency of administration.

In a preferred embodiment, the disease or disorder in which expression levels of the DREAM protein are altered is selected from neurodegenerative disorders, cognitive disorders, sensory perception disorders, inflammatory response disorders and auto inflammatory diseases.

In a more preferred embodiment, the disease or disorder in which expression levels of the DREAM protein are altered is selected from Alzheimer's disease and other types of dementia, schizophrenia, Huntington's disease, dyskinesia, depression, disorders linked to Down's syndrome, chronic pain, neuropathic pain, allodynia, atherosclerosis, type-2 diabetes, rheumatoid arthritis, gout or acute respiratory distress syndrome.

The pharmaceutical compounds and compositions of this invention can be used with other drugs to provide a combined therapy. The other drugs may form part of the same composition or may be provided as a separate composition for administration thereof at the same time or at different times.

Throughout the description and the claims, the word "comprises" and its variants are not intended to exclude other technical characteristics, additives, components or steps. For those skilled in the art, other objects, advantages and characteristics of the invention may be deduced from both the description and the practical use of the invention. The following examples and drawings are provided by way of illustration, and are not meant to limit the present invention.

EXAMPLES

Figure 1:
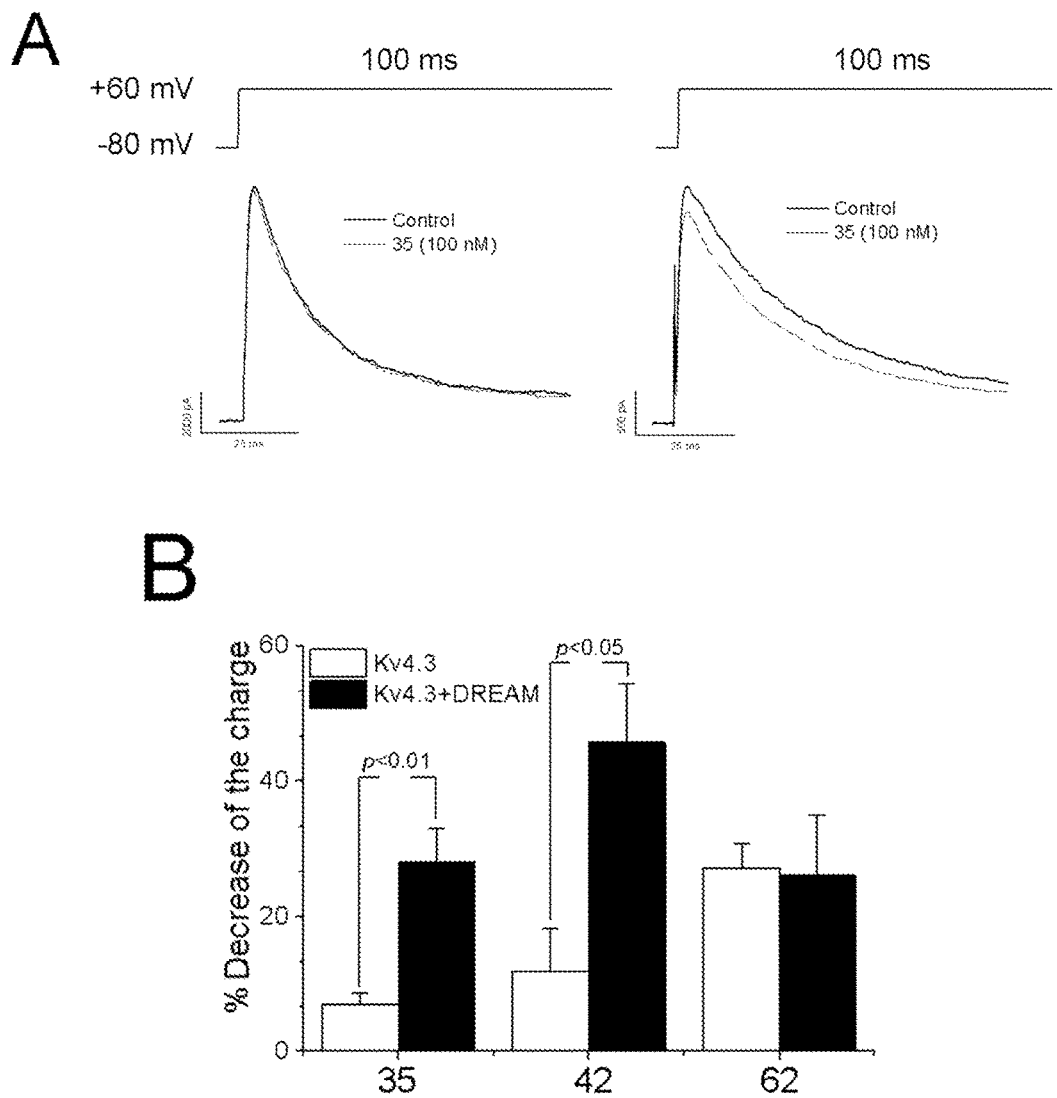
FIG. 1. A: Shows the representative example of the currents generated after the activation of Kv4.3 or Kv4.3+DREAM channels in the absence (black line) and presence (grey line) of the compound (35) at 100 nM. B: shows the bar chart in which the inhibitory effect of the Kv4.3 and Kv4.3+DREAM current produced by (35), (42) and (62) at 100 nM is compared.

The invention is illustrated below by means of tests carried out by the inventors, which reveal the effectiveness of the product of the invention.

Example 1: Synthesis of the Compounds of the Invention. General Procedure

The compounds of general formula (I) of the present invention can be synthesised in two steps following the general methods A-D. In methods A-C, the first step consists in the formation of the necessary acid chlorides; and the second, in the generation of the amide, by reaction of the different acid chlorides and the amine of interest. Method D consists of the use of peptide coupling agents. These methods are described in detail below:

Method A 2.4 mmol of oxalyl chloride and a drop of DMF as a catalyst are added to a solution of the corresponding carboxylic acid (1 mmol) in anhydrous THF (3 ml) at 0° C. The reaction mixture is stirred for two hours at room temperature. The acid chloride formed is dissolved in anhydrous THF (3 mL) and the corresponding amine (1.1 mmol) is added. Then 3 equivalents of anhydrous $Et_3N$ (3 mmol) are added, drop-by-drop, at 0° C. and stirred overnight at room temperature. The solvent is removed in a vacuum and the crude reaction product is suspended in water, it is acidified with 1N HCl to pH=3 or 4, extracted with AcOEt and washed with a solution saturated with NaCl (3×15 mL). The organic phase is dried over $NA_2SO_4$ and concentrated in a vacuum. As indicated in each case, the resulting residue is purified by medium pressure chromatography or crystallisation.

Method B

The procedure for synthesising acid chloride is that which is described in method A. The formation of the amide is carried out by microwave heating at 100° C. for 5 min using THF as a solvent.

Method C

A solution of the corresponding carboxylic acid (0.75 mmol) in thionyl chloride (1.5 mL) is heated under reflux for 6 h. After this time, excess thionyl chloride is evaporated to dryness. The residue is then dissolved in anhydrous THF (2 mL), and the corresponding amine (0.5 mmol) and propylene oxide (7.5 mmol) are added to the solution. The reaction is stirred at room temperature overnight. Finally, the excess solvent is removed in a vacuum and the solid formed is washed with water. The synthesised product is purified by successive washings with the appropriate solvent or by medium pressure chromatography.

Method D 2.2 mmol of DIPEA or NMM are added to a solution of the corresponding amine (0.7 mmol) in DMF (2 mL). The solution is stirred at room temperature for 10 min. A coupling reagent (1.1 mmol, HATU, COMU, PyAOP-HOAt, EDC, DIC, HOBt) and the corresponding acid (1.1 mmol) are then added. After 12 hours of stirring at room temperature, the solvent is removed under reduced pressure. The reaction crude is suspended in water, acidified with 1N HCl to pH=3 or 4, extracted with AcOEt (3×15 mL) and washed with a solution saturated with NaCl (3×15 mL). The organic phase is dried over $NA_2SO_4$ and the solvent is evaporated to dryness. The resulting residue is purified by medium pressure chromatography.

Functionalisation of the Aryl Ring. General Procedure.

Cross coupling technology enables functionalising an aryl ring through reactions catalysed by a transition metal. For example, a Suzuki coupling may be carried out using aryl bromide and a boronic acid coupling partner. Alternatively, couplings can be carried out between an acetylene terminal and an aryl halide by Sonogashira reaction.

a. Suzuki Coupling.

An aryl halide (0.4 mmol), the corresponding derivative of boronic acid (0.6 mmol), $K_2CO_3$ (2.6 mmol), [Pd(PPh$_3$)$_4$] (2% by weight) and 7 mL of a THF/H$_2$O (4/1) mixture are added in a microwave tube. The reaction mixture is purged with argon and heated by irradiating at 125° C. for 15 min in a microwave reactor. Then, a further 0.6 mmol of the corresponding boronic acid is added and the procedure described is repeated. The solvent is removed to dryness, water is added and extracted with DCM (3×10 mL). The organic phases are washed with $H_2O$ (3×10 mL), they are dried over $Na_2SO_4$, and are concentrated under reduced pressure. The crude reaction product is purified by medium pressure chromatography.

b. Sonogashira Reaction

The corresponding brominated derivative (0.22 mmol), CuI (0.06 mmol), [Pd(PPh$_3$)$_4$] (20% by weight), Et$_3$N (1.74 mmol), trimethylsilylalkyne (0.67 mmol) and 1.5 of a THF/DMF mixture (10/3) are added to a sealed 25 mL tube. The reaction mixture is heated at 45° C. for 12 hours. The solvent is evaporated to dryness and the residue is extracted with AcOEt (3×10 mL). The organic phases are washed with $H_2O$ (3×10 mL), dried over $Na_2SO_4$, and concentrated under reduced pressure. The crude reaction product is purified by medium pressure chromatography (hexane/AcOEt).

Saponification of the Ester Group. General Procedure.

A solution of NaOH 2N (0.2 mL) is added, drop-by-drop, to a solution of the corresponding ester (0.09 mmol) in 1.2 mL of THF and 0.6 mL of MeOH. After 12 hours of stirring at room temperature, the solvent is removed under reduced pressure, water is added and acidified with 1N HCl at pH 3 or 4. The aqueous phase is extracted with AcOEt (3×10 mL). The organic extracts are washed with water and solution saturated with NaCl, dried over $Na_2SO_4$, the solvent is removed to dryness and lyophilised. The product is obtained pure without the need for further purification.

Detailed Description of the New Prepared Compounds:

2-[2-(3,4-dichlorophenyl)acetylamino]-4-methoxy-benzoic acid. (7)

White amorphous solid. Yield 60%. $^1$H-NMR (300 MHz, DMSO-d$_6$) δ: 3.78 (3H, s), 3.71 (2H, s), 6.69 (1H, dd, J=8.9, 2.6 Hz), 7.34 (1H, dd, J=8.3, 2.1 Hz), 7.60 (1H, d, J=8.3 Hz), 7.65 (1H, d, J=2.1 Hz), 7.90 (1H, d, J=8.9 Hz), 8.18 (1H, d, J=2.6 Hz), 11.33 (1H, s), 13.26 (1H, s). $^{13}$C-NMR (75 MHz, DMSO-d$_6$) δ: 43.0, 55.4, 104.4, 108.3, 108.6, 129.6, 130.2, 130.5, 130.9, 131.8, 132.9, 135.7, 142.7, 163.5, 168.9, 169.2. LC-MS (m/z): 354.4 ([M+H]$^+$).

4-chloro-2-[2-(3-phenoxyphenyl)acetylamino]benzoic acid. (9)

White crystalline solid. Yield 16%. $^1$H-NMR (300 MHz, DMSO-d$_6$) δ: 3.80 (2H, s), 6.93 (1H, ddd, J=8.2, 2.5, 0.9 Hz), 7.02 (3H, m), 7.12 (2H, m), 7.21 (1H, dd, J=8.6, 2.2 Hz), 7.36 (3H, m), 7.96 (1H, d, J=8.6 Hz), 8.63 (1H, d, J=2.2 Hz), 11.21 (1H, s), 13.87 (1H, s). $^{13}$C-NMR (75 MHz, DMSO-d$_6$) δ: 44.5, 115.3, 118.9, 119.4, 120.4, 123.0, 123.7, 125.3, 130.4, 130.6, 133.2, 136.8, 138.8, 142.1, 157.1, 169.0, 170.2. LC-MS (m/z): 382.5 ([M+H]$^+$).

4-chloro-2-[2-(4-chloro-2-fluorophenyl)acetylamino]benzoic acid. (10)

White crystalline solid. Yield 24%. $^1$H-NMR (300 MHz, DMSO-d$_6$) δ: 3.86 (2H, s), 7.20 (1H, dd, J=8.6, 2.2 Hz), 7.25 (1H, m), 7.32 (1H, m), 7.36 (1H, m), 7.94 (1H, d, J=8.6 Hz), 8.59 (1H, d, J=2.2 Hz), 11.16 (1H, s), 13.85 (1H, s). $^{13}$C-NMR (75 MHz, DMSO-d$_6$) δ: 43.1, 114.7 (d, J=25.1 Hz), 115.1, 115.8 (d, J=21.7 Hz), 119.2, 122.7, 126.2, 132.7, 133.8 (d, J=11.3 Hz), 138.4, 138.6 (d, J=9.0 Hz), 141.5, 162.0 (d, J=247.0 Hz), 168.6, 168.9. LC-MS: 342.3 ([M+H]$^+$).

4-chloro-2-[2-(3,4-dichlorophenyl)acetylamino] methyl benzoate. (13)

White amorphous solid. Yield 55%. $^1$H-NMR (300 MHz, DMSO-d$_6$) δ: 3.79 (3H, s), 3.82 (2H, s), 7.25 (1H, dd, J=8.6, 2.2 Hz), 7.33 (1H, dd, J=8.3, 2.0 Hz), 7.60 (1H, d, J=8.3 Hz), 7.63 (1H, d, J=2.0 Hz), 7.88 (1H, d, J=8.6 Hz), 8.33 (1H, d, J=2.2 Hz), 10.7 (1H, s). $^{13}$C-NMR (75 MHz, DMSO-d$_6$) δ: 43.1, 55.2, 117.1, 121.1, 124.0, 130.4, 130.7, 131.2, 131.6, 132.4, 133.0, 136.5, 139.0, 141.1, 167.4, 169.7. LC-MS (m/z): 324.2 ([M+H]$^+$).

N-(2-benzoylphenyl)-2-(3,4-dichlorophenyl) acetamide. (63)

White amorphous solid. Yield 35%. $^1$H-NMR (300 MHz, DMSO-d$_6$) δ: 3.41 (2H, s), 7.02 (1H, dd, J=8.3, 2.1 Hz), 7.27 (1H, td, J=7.7, 1.0 Hz), 7.32 (1H, d, J=2.1 Hz), 7.37 (1H, dd, J=7.7, 1.5 Hz), 7.42 (2H, td, J=7.7, 1.0 Hz), 7.47 (1H, d, J=8.3 Hz), 7.51 (1H, dd, J=7.7, 1.0 Hz), 7.55 (1H, dd, J=7.7, 1.0 Hz), 7.59 (2H, m), 10.24 (1H, s). $^{13}$C-NMR (75 MHz, DMSO-d$_6$) δ: 41.8, 124.5, 125.3, 124.0, 128.8, 129.9, 130.1, 130.2, 130.5, 130.9, 131.3, 131.8, 131.9, 132.4, 133.3, 136.4, 136.9, 137.6, 168.7, 195.6. LC-MS (m/z): 384.2 ([M+H]$^+$).

4-chloro-2-[2-(3,4-dihydroxyphenyl)acetylamino] benzoic acid. (15)

White amorphous solid. Yield 52%. $^1$H-NMR (400 MHz, DMSO-d$_6$) δ: 3.56 (2H, s), 6.59 (1H, dd, J=8.0, 2.1 Hz), 6.69 (1H, d, J=8.0 Hz), 6.71 (1H, d, J=2.1 Hz), 7.19 (1H, dd, J=8.5, 2.2 Hz), 7.95 (1H, d, J=8.5 Hz), 8.67 (1H, d, J=2.2 Hz), 8.85 (1H, s), 8.92 (1H, s), 11.36 (1H, s). $^{13}$C-NMR (100 MHz, DMSO-d$_6$) δ: 45.2, 116.4, 117.4, 119.4, 121.1, 123.1, 125.6, 133.5, 139.0, 142.7, 145.1, 146.0, 169.4, 171.5. LC-MS (m/z): 322.1 ([M+H]$^+$).

4-chloro-2-[3-(3,4-dichlorophenyl)propanoylamino] benzoic acid. (16)

White amorphous solid. Yield 22%. $^1$H-NMR (300 MHz, DMSO-d$_6$) δ: 2.74 (2H, t, J=7.4 Hz), 2.89 (2H, t, J=7.4 Hz), 7.17 (1H, dd, J=8.6, 2.2 Hz), 7.24 (1H, td, J=8.3, 2.1 Hz), 7.49 (1H, d, J=8.3 Hz), 7.53 (1H, d, J=2.1 Hz), 7.93 (1H, d, J=8.6 Hz), 8.54 (1H, d, J=2.2 Hz), 11.19 (1H, s). $^{13}$C-NMR (75 MHz, DMSO-d$_6$) δ: 29.9, 38.7, 115.7, 119.8, 123.2, 129.3, 129.6, 131.0, 131.4, 133.5, 139.1, 142.3, 142.6, 169.1, 171.3. LC-MS (m/z): 372.1 ([M+H]$^+$).

4-chloro-2-[2-(3,4-dichlorophenyl)acetylamino]-N-methylbenzamide. (21)

White amorphous solid. Yield 23% $^1$H-NMR (400 MHz, DMSO-d$_6$) δ: 2.76 (3H, d, J=4.5 Hz), 3.80 (2H, s), 7.23 (1H, dd, J=8.5, 2.2 Hz), 7.33 (1H, dd, J=8.3, 2.1 Hz), 7.60 (1H, d, J=8.3 Hz), 7.63 (1H, d, J=2.1 Hz), 7.71 (1H, d, J=8.5 Hz), 8.45 (1H, d, J=2.2 Hz), 8.76 (1H, d, J=4.5 Hz), 11.51 (1H, s). $^{13}$C-NMR (100 MHz, DMSO-d$_6$) δ: 26.9, 43.2, 120.3, 120.4, 123.6, 130.3, 130.7, 131.1, 131.5, 132.4, 136.7, 136.7, 140.5, 168.2, 169.5. LC-MS (m/z): 371.1 ([M+H]$^+$).

3-[2-(3-phenoxyphenyl)acetylamino]-2-naphthoic acid. (22)

White amorphous solid. Yield 61%. $^1$H-NMR (400 MHz, DMSO-d$_6$) δ: 3.79 (2H, s), 6.92 (1H, ddd, J=8.2, 2.5, 0.9 Hz), 7.01 (2H, m), 7.05 (1H, t, J=2.5 Hz), 7.10 (1H, tt, J=7.7, 1.1 Hz), 7.15 (1H, dt, J=8.2, 0.9 Hz), 7.36 (3H, m), 7.45 (1H, ddd, J=8.1, 6.9, 1.1 Hz), 7.58 (1H, ddd, J=8.1, 6.9, 1.1 Hz), 7.84 (1H, d, J=8.1 Hz), 7.99 (1H, d, J=8.1 Hz), 8.65 (1H, s), 8.92 (1H, s), 11.11 (1H, s). $^{13}$C-NMR (100 MHz, DMSO-d$_6$) δ: 44.3, 116.6, 117.3, 117.4, 118.5, 120.0, 123.4, 124.9, 125.6, 127.1, 128.2, 129.1, 129.3, 130.0, 130.2, 133.1, 135.5, 136.0, 137.0, 156.7, 169.3, 169.4. LC-MS (m/z): 398.2 ([M+H]$^+$).

3-[3-(3-(3,4-dichlorophenyl)propanoylamino)]-2-naphthoic acid. (23)

White amorphous solid. Yield 71%. $^1$H-NMR (400 MHz, DMSO-d$_6$) δ: 2.79 (2H, s), 2.97 (2H, s), 7.30 (1H, dd, J=8.3; 2.0 Hz), 7.47 (1H, td, J=8.1, 6.9 Hz), 7.53 (1H, t, J=8.3 Hz), 7.59 (1H, m), 7.86 (1H, d, J=8.1 Hz), 8.01 (1H, d, J=8.1 Hz), 8.67 (1H, s), 8.88 (1H, s), 11.15 (1H, s). $^{13}$C-NMR (100 MHz, DMSO-d$_6$) δ: 29.6, 38.2, 116.7, 117.7, 125.5, 127.1, 128.2, 128.6, 129.0, 129.2, 130.4, 130.5, 130.8, 133.1, 135.5, 135.9, 142.3, 169.5, 170.1. LC-MS (m/z): 388.2 ([M+H]$^+$).

4-bromo-2-[2-(3,4-diclorophenyl)acetylamino]benzoic acid. (32)

White amorphous solid. Yield 69%. $^1$H-NMR (400 MHz, DMSO-d$_6$) δ: 3.85 (2H, s), 7.36 (2H, dd, J=8.4, 2.0 Hz), 7.61 (1H, d, J=8.4 Hz), 7.66 (1H, d, J=2.0 Hz), 7.87 (1H, d, J=8.4 Hz), 8.74 (1H, d, J=2.0 Hz), 11.15 (1H, s). $^{13}$C-NMR (100 MHz, DMSO-d$_6$) δ: 42.8, 116.2, 122.2, 125.8, 127.5, 129.8, 130.3, 130.6, 131.0, 131.9, 132.9, 135.6, 141.6, 168.8, 169.2. LC-MS (m/z): 403.0 ([M+H]$^+$).

2-[2-(3,4-dichlorophenyl)acetylamino]-4-ethynyl-benzoic acid. (46)

White amorphous solid. Yield 35%. $^1$H-NMR (500 MHz, DMSO-d$_6$) δ: 3.84 (2H, s), 4.44 (1H, s), 7.22 (1H, dd, J=8.1, 1.6 Hz), 7.36 (1H, dd, J=8.3, 2.1 Hz), 7.61 (1H, d, J=8.2 Hz), 7.66 (1H, d, J=2.1 Hz), 7.92 (1H, d, J=8.1 Hz), 8.57 (1H, d, J=1.6 Hz), 11.24 (1H, s). $^{13}$C-NMR (125 MHz, DMSO-d$_6$) δ: 42.8, 82.6, 83.5, 122.7, 125.8, 126.7, 129.7, 130.2, 130.6, 130.9, 131.4, 131.8, 135.8, 140.5, 168.7, 169.0. LC-MS (m/z): 348.1 ([M+H]$^+$).

2-[2-(3,4-dichlorophenyl)acetylamino]-methyl 5-phenylbenzoate. (48)

White amorphous solid. Yield 80%. $^1$H-NMR (400 MHz, DMSO-d$_6$) δ: 3.82 (3H, s), 3.83 (2H, s), 7.38 (2H, m), 7.47 (2H, m), 7.63 (1H, d, J=8.3 Hz), 7.67 (3H, m), 7.92 (1H, dd, J=8.7, 2.3 Hz), 8.12 (1H, d, J=2.3 Hz), 8.25 (1H, d, J=8.7 Hz), 10.64 (1H, s). $^{13}$C-NMR (100 MHz, DMSO-d$_6$) δ: 42.4, 52.4, 119.2, 122.2, 126.4, 127.7, 128.2, 129.1, 129.6, 130.0, 130.5, 130.9, 131.6, 131.8, 135.2, 136.3, 138.2, 138.5, 167.3, 168.7. LC-MS (m/z): 414.2 ([M+H]$^+$).

2-[2-(3,4-dichlorophenyl)acetylamino]-5-(2'-methyl-phenyl)methyl benzoate. (49)

White amorphous solid. Yield 84%. $^1$H-NMR (400 MHz, DMSO-d$_6$) δ: 2.21 (3H, s), 3.78 (3H, s), 3.83 (2H, s), 7.20 (1H, m), 7.28 (3H, m), 7.37 (1H, dd, J=8.3, 2.0 Hz), 7.60 (1H, dd, J=8.5, 2.2 Hz), 7.63 (1H, d, J=8.3 Hz), 7.67 (1H, d, J=2.0 Hz), 7.78 (1H, d, J=2.2 Hz), 8.22 (1H, d, J=8.5 Hz), 10.64 (1H, s). $^{13}$C-NMR (100 MHz, DMSO-d$_6$) δ: 20.1, 42.4, 52.4, 118.6, 121.4, 126.1, 127.7, 129.4, 129.6, 130.0, 130.4, 130.5, 130.6, 130.9, 131.6, 134.2, 134.8, 140.2, 136.3, 137.8, 139.7, 167.2, 168.7. LC-MS (m/z): 428.3 ([M+H]$^+$).

2-[2-(3,4-dichlorophenyl)acetylamino]-5-(4'-tert-butylphenyl)methyl benzoate. (50)

White amorphous solid. Yield 63%. $^1$H-NMR (400 MHz, DMSO-d$_6$) δ: 1.30 (9H, s), 3.81 (2H, s), 7.36 (1H, dd, J=8.2, 2.0 Hz), 7.48 (2H, d, J=8.6 Hz), 7.58 (2H, d, J=8.6 Hz), 7.62 (1H, d, J=8.2 Hz), 7.65 (1H, d, J=2.0 Hz), 7.88 (1H, dd, J=8.6, 2.3 Hz), 8.08 (1H, d, J=2.3 Hz), 8.20 (1H, d, J=8.6 Hz), 10.61 (1H, s). $^{13}$C-NMR (100 MHz, DMSO-d$_6$) δ: 31.1, 34.4, 42.5, 52.5, 119.5, 122.4, 126.0, 126.2, 128.1, 129.7, 130.1, 130.6, 131.0, 131.6, 131.7, 135.6, 135.7, 136.4, 138.0, 150.3, 167.4, 168.8. LC-MS (m/z): 470.3 ([M+H]$^+$).

2-[2-(3,4-dichlorophenyl)acetylamino]-5-(4'-n-butyl-phenyl)methyl benzoate. (51)

White amorphous solid. Yield 67%. $^1$H-NMR (400 MHz, DMSO-d$_6$) δ: 0.90 (3H, t, J=7.3 Hz), 1.32 (2H, sx, J=7.3 Hz), 1.96 (2H, q, J=7.3 Hz), 2.61 (2H, t, J=7.3 Hz), 3.82 (3H, s), 3.82 (2H, s), 7.29 (2H, d, J=8.4 Hz), 7.36 (1H, dd, J=8.2, 2.0 Hz), 7.57 (2H, d, J=8.4 Hz), 7.64 (1H, d, J=8.2 Hz), 7.66 (1H, d, J=2.0 Hz), 7.89 (1H, dd, J=8.7, 2.3 Hz), 8.09 (1H, d, J=2.3 Hz), 8.23 (1H, d, J=8.7 Hz), 10.62 (1H, s). $^{13}$C-NMR (100 MHz, DMSO-d$_6$) δ: 13.8, 21.7, 33.1, 34.1, 42.4, 52.4, 119.2, 122.2, 126.2, 127.9, 129.0, 129.6, 130.0, 130.5, 130.9, 131.5, 131.6, 135.2, 135.8, 136.3, 138.0, 142.0, 167.3, 168.6. LC-MS (m/z): 470.2 ([M+H]$^+$).

2-[2-(3,4-dichlorophenyl)acetylamino]-methyl 4-phenylbenzoate. (52)

White amorphous solid. Yield 71%. $^1$H-NMR (400 MHz, DMSO-d$_6$) δ: 3.83 (3H, s), 3.85 (2H, s), 7.37 (1H, dd, J=8.3, 2.0 Hz), 7.44 (1H, m), 7.51 (3H, m), 7.62 (1H, d, J=8.3 Hz), 7.67 (3H, m), 7.98 (1H, d, J=8.3 Hz), 8.56 (1H, d, J=1.8 Hz), 11.73 (1H, s). $^{13}$C-NMR (100 MHz, DMSO-d$_6$) δ: 43.1, 53.0, 117.5, 119.9, 122.4, 127.5, 129.3, 129.8, 130.3, 130.8, 131.2, 131.5, 131.9, 132.4, 136.8, 139.3, 140.5, 146.0, 167.9, 169.6. LC-MS (m/z): 414.1 ([M+H]$^+$).

2-[2-(3,4-dichlorophenyl)acetylamino]-4-(2'-methyl-phenyl)methyl benzoate. (53)

White amorphous solid. Yield 47%. $^1$H-NMR (400 MHz, DMSO-d$_6$) δ: 2.23 (3H, s), 3.82 (5H, s), 7.19 (1H, dd, J=8.1, 1.8 Hz), 7.20 (1H, m), 7.28 (1H, m), 7.32 (2H, m), 7.35 (1H, dd, J=8.2, 1.9 Hz), 7.61 (1H, d, J=8.2 Hz), 7.65 (1H, d, J=1.9 Hz), 7.95 (1H, d, J=8.1 Hz), 8.20 (1H, d, J=1.8 Hz), 10.70 (1H, s). $^{13}$C-NMR (100 MHz, DMSO-d$_6$) δ: 20.1, 42.5, 52.4, 116.6, 121.8, 126.2, 126.2, 128.1, 129.2, 129.6, 130.1, 130.5, 130.6, 130.9, 131.7, 134.6, 136.2, 139.1, 140.0, 146.7, 167.3, 168.9. LC-MS (m/z): 428.3 ([M+H]$^+$).

2-[2-(3,4-dichlorophenyl)acetylamino]-4-(4'-n-butyl-phenyl)methyl benzoate. (54)

White amorphous solid. Yield 72%. $^1$H-NMR (400 MHz, DMSO-d$_6$) δ: 0.90 (3H, t, J=7.3 Hz), 1.31 (2H, sx, J=7.3

Hz), 1.57 (2H, q, J=7.3 Hz), 2.62 (2H, t, J=7.3 Hz), 3.83 (3H, s), 3.85 (2H, s), 7.32 (1H, d, J=8.4 Hz), 7.37 (1H, dd, J=8.3, 2.1 Hz), 7.49 (1H, dd, J=8.3, 1.9 Hz), 7.58 (2H, d, J=8.4 Hz), 7.62 (1H, d, J=8.3 Hz), 7.67 (1H, d, J=2.1 Hz), 7.96 (1H, d, J=8.3 Hz), 8.55 (1H, d, J=1.9 Hz), 10.73 (1H, s). $^{13}$C-NMR (100 MHz, DMSO-d$_6$) δ: 13.8, 21.8, 33.0, 34.5, 42.5, 52.4, 116.4, 118.9, 121.4, 126.8, 129.1, 129.6, 130.1, 130.5, 130.9, 131.2, 131.7, 136.0, 136.2, 139.9, 143.1, 145.3, 167.3, 168.9. LC-MS (m/z): 470.2 ([M+H]$^+$).

2-[3-(3,4-dichlorophenyl)propanoylamino]-methyl 5-phenylbenzoate. (55)

White amorphous solid. Yield 62%. $^1$H-NMR (400 MHz, DMSO-d$_6$) δ: 2.76 (2H, t, J=7.5 Hz), 2.94 (2H, t, J=7.5 Hz), 3.86 (3H, s), 7.28 (1H, dd, J=8.2, 2.0 Hz), 7.38 (1H, t, J=7.6 Hz), 7.48 (2H, t, J=7.6 Hz), 7.53 (1H, d, J=8.2 Hz), 7.57 (1H, d, J=2.0 Hz), 7.66 (2H, d, J=7.6 Hz), 7.91 (1H, dd, J=8.7, 2.3 Hz), 8.12 (1H, d, J=2.3 Hz), 8.27 (1H, d, J=8.7 Hz), 10.54 (1H, s). $^{13}$C-NMR (100 MHz, DMSO-d$_6$) δ: 29.7, 37.9, 52.6, 118.7, 122.0, 126.4, 127.7, 128.2, 128.7, 129.0, 129.2, 130.4, 130.5, 130.9, 131.9, 135.0, 138.6, 142.2, 167.4, 170.4. LC-MS (m/z): 428.2 ([M+H]$^+$).

2-[3-(3,4-dichlorophenyl)propanoylamino]-5-(2'-methylphenyl)methyl benzoate. (56)

White amorphous solid. Yield 99%. $^1$H-NMR (400 MHz, DMSO-d$_6$) δ: 2.22 (3H, s), 2.77 (2H, t, J=7.5 Hz), 2.95 (2H, t, J=7.5 Hz), 3.83 (2H, s), 7.20 (1H, m), 7.28 (4H, m), 7.54 (1H, d, J=8.2 Hz), 7.58 (1H, d, J=2.0 Hz), 7.59 (1H, dd, J=8.6, 2.1 Hz), 7.79 (1H, d, J=2.1 Hz), 8.25 (1H, d, J=8.6 Hz), 10.55 (1H, s). $^{13}$C-NMR (100 MHz, DMSO-d$_6$) δ: 20.1, 29.6, 37.9, 52.5, 118.0, 121.2, 126.1, 127.7, 128.6, 129.0, 129.5, 130.4, 130.5, 130.5, 130.6, 130.8, 134.3, 134.8, 136.0, 138.0, 139.7, 142.2, 167.4, 170.3. LC-MS (m/z): 442.2 ([M+H]$^+$).

2-[3-(3,4-dichlorophenyl)propanoylamino]-5-(4'-n-butylphenyl)methyl benzoate. (57)

White amorphous solid. Yield 81%. $^1$H-NMR (400 MHz, DMSO-d$_6$) δ: 0.90 (3H, t, J=7.3 Hz), 1.32 (2H, sx, J=7.3 Hz), 1.56 (2H, q, J=7.3 Hz), 2.61 (2H, t, J=7.3 Hz), 2.76 (2H, t, J=7.5 Hz), 2.94 (2H, t, J=7.5 Hz), 3.86 (3H, s), 7.28 (1H, dd, J=8.2, 2.4 Hz), 7.29 (2H, d, J=8.2 Hz), 7.54 (1H, d, J=8.2 Hz), 7.56 (1H, d, J=2.4 Hz), 7.57 (2H, d, J=8.2 Hz), 7.89 (1H, dd, J=8.7, 2.3 Hz), 8.10 (1H, d, J=2.3 Hz), 8.26 (1H, d, J=8.7 Hz), 10.53 (1H, s). $^{13}$C-NMR (100 MHz, DMSO-d$_6$) δ: 13.8, 21.8, 29.6, 33.2, 34.4, 37.9, 52.5, 118.6, 121.9, 126.2, 129.7, 128.6, 128.9, 129.0, 130.4, 130.5, 130.8, 131.7, 134.9, 135.9, 138.3, 141.9, 142.2, 167.4, 170.2. LC-MS (m/z): 484.4 ([M+H]$^+$).

2-[3-(3,4-dichlorophenyl)propanoylamino]-methyl 4-phenylbenzoate. (58)

White amorphous solid. Yield 70%. $^1$H-NMR (400 MHz, DMSO-d$_6$) δ: 2.78 (2H, t, J=7.4 Hz), 2.95 (2H, t, J=7.4 Hz), 3.86 (3H, s), 7.28 (1H, dd, J=8.3, 2.0 Hz), 7.45 (1H, tt, J=7.4, 1.3 Hz), 7.50 (4H, m), 7.58 (1H, d, J=2.0 Hz), 7.67 (2H, dd, J=8.3, 1.3 Hz), 7.98 (1H, d, J=8.3 Hz), 8.56 (1H, d, J=1.8 Hz), 10.63 (1H, s). $^{13}$C-NMR (100 MHz, DMSO-d$_6$) δ: 29.6, 38.0, 52.5, 116.4, 119.1, 121.5, 126.9, 128.6, 128.9, 129.2, 130.4, 130.5, 130.5, 130.8, 131.3, 138.8, 140.1, 142.1, 145.4, 167.4, 170.5. LC-MS (m/z): 428.3 ([M+H]$^+$).

2-[3-(3,4-dichlorophenyl)propanoylamino]-4-(2'-methylphenyl)methyl benzoate. (59)

White amorphous solid. Yield 67%. $^1$H-NMR (400 MHz, DMSO-d$_6$) δ: 2.24 (3H, s), 2.76 (2H, t, J=7.5 Hz), 2.93 (2H, t, J=7.5 Hz), 3.86 (3H, s), 7.17 (1H, dd, J=8.1, 1.8 Hz), 7.21 (1H, d, J=7.9 Hz), 7.27 (1H, dd, J=8.3, 2.0 Hz), 7.30 (1H, m), 7.32 (2H, m), 7.52 (1H, d, J=8.3 Hz), 7.56 (1H, d, J=2.0 Hz), 7.96 (1H, d, J=8.1 Hz), 8.23 (1H, d, J=1.8 Hz), 10.62 (1H, s). $^{13}$C-NMR (100 MHz, DMSO-d$_6$) δ: 20.1, 29.5, 37.9, 52.4, 116.1, 121.6, 123.9, 126.1, 128.1, 128.6, 128.9, 129.1, 130.4, 130.5, 130.5, 130.6, 130.8, 134.6, 139.4, 140.0, 142.1, 146.7, 167.4, 170.4. LC-MS (m/z): 442.2 ([M+H]$^+$).

2-[3-(3,4-dichlorophenyl)propanoylamino]-4-(4'-n-butylphenyl)methyl benzoate. (60)

White amorphous solid. Yield 78%. $^1$H-NMR (400 MHz, DMSO-d$_6$) δ: 0.91 (3H, t, J=7.3 Hz), 1.32 (2H, sx, J=7.3 Hz), 1.58 (2H, q, J=7.3 Hz), 2.63 (2H, t, J=7.3 Hz), 2.78 (2H, t, J=7.5 Hz), 2.95 (2H, t, J=7.5 Hz), 3.86 (3H, s), 7.29 (1H, dd, J=8.2, 2.0 Hz), 7.33 (2H, d, J=8.3 Hz, 2H), 7.47 (1H, dd, J=8.3, 1.9 Hz), 7.53 (1H, d, J=8.2 Hz), 7.58 (2H, d, J=8.3 Hz), 7.58 (1H, d, J=2.0 Hz), 7.97 (1H, d, J=8.3 Hz), 8.57 (1H, d, J=1.9 Hz), 10.64 (1H, s). $^{13}$C-NMR (100 MHz, DMSO-d$_6$) δ: 13.8, 21.8, 29.6, 33.0, 34.5, 37.9, 52.4, 115.9, 118.7, 121.1, 126.7, 128.6, 128.9, 129.1, 130.4, 130.5, 130.8, 131.2, 136.1, 140.1, 142.1, 143.1, 145.3, 167.4, 170.4. LC-MS (m/z): 484.3 ([M+H]$^+$).

2-[2-(3,4-dichlorophenyl)acetylamino]-5-phenylbenzoic acid. (42)

White amorphous solid. Yield 91%. $^1$H-NMR (400 MHz, DMSO-d$_6$) δ: 3.86 (2H, s), 7.38 (2H, m), 7.47 (2H, m), 7.62 (1H, d, J=8.2 Hz), 7.67 (3H, m), 7.91 (1H, dd, J=8.7, 2.4 Hz), 8.20 (1H, d, J=2.4 Hz), 8.56 (1H, d, J=8.7 Hz), 11.14 (1H, s). $^{13}$C-NMR (100 MHz, DMSO-d$_6$) δ: 42.9, 117.4, 120.7, 126.3, 127.6, 128.7, 129.1, 129.7, 130.2, 130.6, 130.9, 131.8, 132.0, 134.5, 136.0, 138.6, 139.8, 168.7, 169.2. LC-MS (m/z): 400.1 ([M+H]$^+$).

2-[2-(3,4-dichlorophenyl)acetylamino]-5-(2'-methylphenyl)benzoic acid. (37)

White amorphous solid. Yield 92%. $^1$H-NMR (400 MHz, DMSO-d$_6$) δ: 2.22 (2H, s), 3.86 (3H, s), 7.20 (1H, m), 7.27 (3H, m), 7.38 (1H, dd, J=8.3, 2.1 Hz), 7.59 (1H, dd, J=8.6, 2.2 Hz), 7.62 (1H, d, J=8.3 Hz), 7.69 (1H, d, J=2.1 Hz), 7.86 (1H, d, J=2.2 Hz), 8.53 (1H, d, J=8.6 Hz), 11.12 (1H, s). $^{13}$C-NMR (100 MHz, DMSO-d$_6$) δ: 20.1, 42.9, 116.7, 120.0, 126.1, 127.6, 129.4, 129.7, 130.2, 130.5, 130.6, 131.0, 131.2, 131.8, 134.5, 134.7, 135.6, 136.0, 139.3, 139.8, 168.7, 169.2. LC-MS (m/z): 414.2 ([M+H]$^+$).

2-[2-(3,4-dichlorophenyl)acetylamino]-5-(4'-tert-butylphenyl)benzoic acid. (36)

White amorphous solid. Yield 96%. $^1$H-NMR (400 MHz, DMSO-d$_6$) δ: 1.30 (9H, s), 3.88 (2H, s), 7.38 (1H, dd, J=8.3, 2.1 Hz), 7.47 (2H, d, J=8.6 Hz), 7.58 (2H, d, J=8.6 Hz), 7.62 (1H, d, J=8.3 Hz), 7.68 (1H, d, J=2.1 Hz), 7.88 (1H, dd, J=8.7, 2.4 Hz), 8.18 (1H, d, J=2.4 Hz), 8.53 (1H, d, J=8.7 Hz), 11.17 (1H, s). $^{13}$C-NMR (100 MHz, DMSO-d$_6$) δ: 31.0, 34.3, 42.9, 118.2, 121.3, 126.5, 126.7, 129.2, 130.3, 130.9, 131.3, 131.6, 132.4, 132.5, 135.0, 136.5, 136.7, 140.2, 150.0, 169.4, 169.9. LC-MS (m/z): 456.1 ([M+H]$^+$).

2-[2-(3,4-dichlorophenyl)acetylamino]-5-(4'-n-butylphenyl)benzoic acid. (34)

White amorphous solid. Yield 92%. $^1$H-NMR (400 MHz, DMSO-d$_6$) δ: 0.90 (3H, t, J=7.3 Hz), 1.31 (2H, sx, J=7.3 Hz), 1.56 (2H, q, J=7.3 Hz), 2.60 (2H, t, J=7.3 Hz), 3.85 (2H, s), 7.27 (2H, d, J=8.3 Hz), 7.38 (1H, dd, J=8.3, 2.0 Hz), 7.56 (2H, d, J=8.3 Hz), 7.62 (1H, d, J=8.3 Hz), 7.68 (1H, d, J=2.0 Hz), 7.88 (1H, dd, J=8.8, 2.4 Hz), 8.17 (1H, d, J=2.4 Hz), 8.54 (1H, d, J=8.8 Hz), 11.10 (1H, s). $^{13}$C-NMR (100 MHz, DMSO-d$_6$) δ: 13.8, 21.8, 33.1, 34.4, 42.9, 117.3, 120.7, 126.2, 128.5, 129.0, 129.7, 130.2, 130.6, 131.0, 131.8, 131.8, 134.5, 136.0, 139.5, 141.8, 168.7, 169.3. LC-MS (m/z): 456.4 ([M+H]$^+$).

2-[2-(3,4-dichlorophenyl)acetylamino]-4-phenylbenzoic acid. (39)

White amorphous solid. Yield 91%. $^1$H-NMR (400 MHz, DMSO-d$_6$) δ: 3.87 (2H, s), 7.38 (1H, dd, J=8.3, 2.0 Hz), 7.44 (1H, m), 7.46 (1H, dd, J=8.2, 1.8 Hz), 7.50 (2H, t, J=7.4 Hz), 7.62 (1H, d, J=8.3 Hz), 7.65 (1H, d, J=2.0 Hz), 7.68 (2H, dd, J=7.4, 1.8 Hz), 8.03 (1H, d, J=8.2 Hz), 8.83 (1H, d, J=1.8 Hz), 11.21 (1H, s). $^{13}$C-NMR (100 MHz, DMSO-d$_6$) δ: 42.9, 115.4, 117.9, 121.1, 126.9, 128.6, 129.1, 129.7, 130.3, 130.5, 130.9, 131.8, 131.9, 135.9, 138.9, 141.1, 145.4, 169.0, 169.2. LC-MS (m/z): 400.1 ([M+H]$^+$).

2-[2-(3,4-dichlorophenyl)acetylamino]-4-(2'-methylphenyl)benzoic acid. (40)

White amorphous solid. Yield 85%. $^1$H-NMR (400 MHz, DMSO-d$_6$) δ: 2.23 (3H, s), 3.84 (2H, s), 7.13 (1H, dd, J=8.1, 1.8 Hz), 7.20 (1H, m), 7.27 (3H, m), 7.36 (1H, dd, J=8.3, 2.1 Hz), 7.61 (1H, d, J=8.3 Hz), 7.67 (1H, d, J=2.1 Hz), 8.01 (1H, d, J=8.1 Hz), 8.49 (1H, d, J=1.8 Hz), 11.20 (1H, s). $^{13}$C-NMR (100 MHz, DMSO-d$_6$) δ: 20.1, 42.9, 115.1, 120.5, 123.5, 126.1, 128.0, 129.1, 129.7, 130.3, 130.5, 130.9, 131.0, 131.9, 134.6, 135.9, 140.2, 140.4, 146.8, 168.9, 169.2. LC-MS (m/z): 414.2 ([M+H]$^+$).

2-[2-(3,4-dichlorophenyl)acetylamino]-4-(4'-n-butylphenyl)benzoic acid. (35)

White amorphous solid. Yield 94%. $^1$H-NMR (400 MHz, DMSO-d$_6$) δ: 0.90 (3H, t, J=7.3 Hz), 1.31 (2H, sx, J=7.3 Hz), 1.57 (2H, q, J=7.3 Hz), 2.62 (2H, t, J=7.3 Hz), 3.87 (2H, s), 7.31 (2H, d, J=8.3 Hz), 7.38 (1H, dd, J=8.3, 2.0 Hz), 7.43 (1H, dd, J=8.3, 1.9 Hz), 7.57 (2H, d, J=8.3 Hz), 7.62 (1H, d, J=8.3 Hz), 7.68 (1H, d, J=2.0 Hz), 8.01 (1H, d, J=8.3 Hz), 8.82 (1H, d, J=1.9 Hz), 11.21 (1H, s). $^{13}$C-NMR (100 MHz, DMSO-d$_6$) δ: 13.8, 21.8, 33.0, 34.5, 42.9, 115.0, 117.6, 120.8, 126.7, 129.1, 129.7, 130.3, 130.6, 130.9, 131.8, 131.9, 135.9, 136.2, 141.2, 143.0, 145.4, 168.9, 169.3. LC-MS (m/z): 456.1 ([M+H]$^+$).

2-[3-(3,4-dichlorophenyl)propanoylamino]-5-phenylbenzoic acid. (61)

White amorphous solid. Yield 99%. $^1$H-NMR (400 MHz, DMSO-d$_6$) δ: 2.76 (2H, t, J=7.5 Hz), 2.93 (2H, t, J=7.5 Hz), 7.27 (1H, dd, J=8.3, 2.1 Hz), 7.35 (1H, tt, J=7.6, 1.1 Hz), 7.45 (2H, t, J=7.6 Hz), 7.51 (1H, d, J=8.3 Hz), 7.56 (1H, d, J=2.1 Hz), 7.64 (2H, dd, J=7.6, 1.1 Hz), 7.88 (1H, dd, J=8.7, 2.4 Hz), 8.19 (1H, d, J=2.4 Hz), 8.52 (1H, d, J=8.7 Hz), 11.20 (1H, s). $^{13}$C-NMR (100 MHz, DMSO-d$_6$) δ: 30.2, 38.4, 117.9, 121.4, 127.0, 128.2, 129.3, 129.4, 129.6, 129.7, 131.0, 131.2, 131.5, 132.7, 134.9, 139.4, 140.5, 142.8, 170.0, 170.9. LC-MS: 414.1 (M+H)+. LC-MS (m/z): 414.2 ([M+H]$^+$).

2-[3-(3,4-dichlorophenyl)propanoylamino]-5-(2'-methylphenyl)benzoic acid. (44)

White amorphous solid. Yield 66%. $^1$H-NMR (400 MHz, DMSO-d$_6$) δ: 2.23 (3H, s), 2.78 (2H, t, J=7.5 Hz), 2.96 (2H, t, J=7.5 Hz), 7.21 (1H, m), 7.29 (4H, m), 7.54 (1H, d, J=8.2 Hz), 7.58 (1H, d, J=2.0 Hz), 7.59 (1H, dd, J=8.5, 2.2 Hz), 7.88 (1H, d, J=2.2 Hz), 8.51 (1H, d, J=8.5 Hz), 11.16 (1H, s), 13.68 (1H, s). $^{13}$C-NMR (100 MHz, DMSO-d$_6$) δ: 20.1, 29.5, 38.1, 116.7, 120.0, 126.1, 127.5, 128.6, 128.9, 129.4, 130.4, 130.4, 130.5, 130.8, 131.1, 134.4, 134.7, 135.3, 139.4, 139.8, 142.1, 169.3, 170.2. LC-MS (m/z): 428.2 ([M+H]$^+$).

2-[3-(3,4-dichlorophenyl)propanoylamino]-5-(4'-tert-butylphenyl)benzoic acid. (43)

White amorphous solid. Yield 91%. $^1$H-NMR (400 MHz, DMSO-d$_6$) δ: 1.31 (3H, s), 2.77 (2H, t, J=7.5 Hz), 2.95 (2H, t, J=7.5 Hz), 7.29 (1H, dd, J=8.3, 2.1 Hz), 7.48 (2H, d, J=8.4 Hz), 7.53 (1H, d, J=8.3 Hz), 7.58 (3H, m), 7.88 (1H, dd, J=8.7, 2.3 Hz), 8.19 (1H, d, J=2.3 Hz), 8.53 (1H, d, J=8.7 Hz), 11.10 (1H, s), 13.70 (1H, s). $^{13}$C-NMR (100 MHz, DMSO-d$_6$) δ: 29.6, 31.2, 34.4, 38.3, 117.2, 120.7, 125.8, 126.0, 128.5, 128.9, 130.4, 130.5, 130.8, 131.9, 134.2, 135.9, 139.6, 142.1, 150.0, 169.3, 170.2. LC-MS (m/z): 470.3 ([M+H]$^+$).

2-[3-(3,4-dichlorophenyl)propanoylamino]-5-(4'-n-butylphenyl)benzoic acid. (38)

White amorphous solid. Yield 91%. $^1$H-NMR (400 MHz, DMSO-d$_6$) δ: 0.90 (3H, t, J=7.3 Hz), 1.32 (2H, sx, J=7.3 Hz), 1.57 (2H, q, J=7.3 Hz), 2.69 (2H, t, J=7.3 Hz), 2.77 (2H, t, J=7.5 Hz), 2.95 (2H, t, J=7.5 Hz), 7.29 (3H, m), 7.53 (1H, d, J=8.3 Hz), 7.56 (2H, d, J=8.2 Hz), 7.58 (1H, d, J=2.0 Hz), 7.88 (1H, dd, J=8.7, 2.3 Hz), 8.19 (1H, d, J=2.3 Hz), 8.53 (1H, d, J=8.7 Hz), 11.10 (1H, s), 13.76 (1H, s). $^{13}$C-NMR (100 MHz, DMSO-d$_6$) δ: 13.8, 21.8, 29.5, 33.1, 34.4, 38.2, 117.2, 120.7, 126.2, 128.5, 128.6, 128.9, 129.0, 130.4, 130.5, 130.8, 131.8, 134.2, 136.1, 139.6, 141.8, 142.2, 169.4, 170.2. LC-MS (m/z): 470.2 ([M+H]$^+$).

2-[3-(3,4-dichlorophenyl)propanoylamino]-4-phenylbenzoic acid. (41)

White amorphous solid. Yield 89%. $^1$H-NMR (400 MHz, DMSO-d$_6$) δ: 2.79 (2H, t, J=7.5 Hz), 2.96 (2H, t, J=7.4 Hz), 7.30 (1H, dd, J=8.3, 2.1 Hz), 7.44 (1H, m), 7.50 (4H, m), 7.58 (1H, d, J=2.1 Hz), 7.67 (2H, dd, J=8.2, 1.3 Hz), 8.05 (1H, d, J=8.3 Hz), 8.81 (1H, d, J=1.8 Hz), 11.20 (1H, s). $^{13}$C-NMR (100 MHz, DMSO-d$_6$) δ: 29.4, 38.2, 115.3, 117.9, 120.9, 126.9, 128.6, 128.7, 128.9, 129.2, 130.4, 130.5, 130.8, 131.8, 139.0, 141.2, 142.1, 145.4, 169.3, 170.4. LC-MS (m/z): 414.2 ([M+H]$^+$).

2-[3-(3,4-dichlorophenyl)propanoylamino]-4-(2'-methylphenyl)benzoic acid. (45)

White amorphous solid. Yield 94%. $^1$H-NMR (400 MHz, DMSO-d$_6$) δ: 2.24 (3H, s), 2.77 (2H, t, J=7.5 Hz), 2.93 (2H, t, J=7.5 Hz), 7.12 (1H, dd, J=8.1, 1.8 Hz), 7.21 (1H, m), 7.29 (2H, dd, J=8.2, 2.1 Hz), 7.32 (2H, m), 7.52 (1H, d, J=8.2 Hz), 7.56 (1H, d, J=2.1 Hz), 8.02 (1H, d, J=8.1 Hz), 8.47 (1H, d, J=1.8 Hz), 11.17 (1H, s). $^{13}$C-NMR (100 MHz, DMSO-$d_6$) δ: 20.1, 29.4, 38.2, 114.9, 120.4, 123.3, 126.1, 128.0, 128.6, 128.9, 129.1, 130.4, 130.5, 130.5, 130.7, 131.0, 134.6, 140.2, 140.0, 140.5, 142.1, 169.3, 170.3. LC-MS (m/z): 428.2 ([M+H]$^+$).

2-[3-(3,4-dichlorophenyl)propanoylamino]-4-(4'-n-butylphenyl)benzoic acid. (64)

White amorphous solid. Yield 89%. $^1$H-NMR (400 MHz, DMSO-$d_6$) δ: 0.90 (3H, t, J=7.3 Hz), 1.32 (2H, sx, J=7.3 Hz), 1.57 (2H, q, J=7.3 Hz), 2.63 (2H, t, J=7.3 Hz), 2.79 (2H, t, J=7.5 Hz), 2.96 (2H, t, J=7.5 Hz), 7.29 (1H, dd, J=8.2, 2.1 Hz), 7.33 (2H, d, J=8.3 Hz), 7.42 (1H, dd, J=8.3, 1.9 Hz), 7.53 (1H, d, J=8.2 Hz), 7.58 (2H, d, J=8.3 Hz), 7.58 (1H, d, J=2.1 Hz), 8.03 (1H, d, J=8.3 Hz), 8.80 (1H, d, J=1.9 Hz), 11.19 (1H, s), 13.59 (1H, s). $^{13}$C-NMR (100 MHz, DMSO-$d_6$) δ: 13.8, 21.8, 29.4, 33.0, 34.5, 38.2, 114.9, 117.6, 120.6, 126.7, 128.6, 128.9, 129.1, 130.4, 130.5, 130.8, 131.8, 136.3, 141.2, 142.1, 143.0, 145.4, 169.3, 170.4. LC-MS (m/z): 470.3 ([M+H]$^+$).

(2R)-2-[2-(3,4-dichlorophenyl)acetylamino]-3-(1-trityl-1H-imidazol-4-yl)methyl propanoate. (62)

White amorphous solid. Yield 71%. $^1$H-NMR (300 MHz, CD$_3$Cl) δ: 2.91 (1H, dd, J=14.7, 4.5 Hz), 3.00 (1H, dd, J=14.7, 5.8 Hz), 3.51 (3H, s), 4.04 (1H, d, J=14.3 Hz), 4.06 (1H, d, J=14.3 Hz), 4.66 (1H, ddd, J=7.8, 5.8, 4.5 Hz), 6.50 (1H, s), 6.99 (6H, m), 7.09 (1H, dd, J=8.2, 2.1 Hz), 7.19 (1H, s), 7.28 (10H, m), 7.37 (1H, d, J=2.1 Hz), 7.68 (1H, d, J=7.8 Hz). $^{13}$C-NMR (75 MHz, CD$_3$Cl) δ: 28.0, 41.0, 51.4, 52.0, 75.0, 119.0, 119.1, 119.3, 127.3, 128.0, 129.0, 129.7, 130.0, 130.5, 131.0, 134.5, 136.5, 141.0, 169.0, 171.0. LC-MS (m/z): 599.1 ([M+H]$^+$).

Example 2. Trials on the Effect of the Compounds of the Invention on the Kv4.3 Channel Modulation by DREAM The new compounds synthesised according to this invention have been evaluated in vitro in voltage-binding assays in CHO cells transiently transfected with cDNA encoding Kv4.3 only or Kv4.3 in the presence of DREAM (Kv4.3+DREAM) using the patch-clamp technique. Some of the compounds inhibit Kv4.3 channel modulation by DREAM. For some of the compounds evaluated, this effect is selective and is only observed in the presence of the DREAM channel modulator. Thus, as shown in FIG. 1B, compounds (35) and (42) only inhibit the Kv4.3 current in the presence of DREAM, measured as the % decrease of the amount of charge passing through the membrane and estimated based on the integral of the current. However, (62) has no selectivity, joining the channel in the absence of DREAM, since it similarly inhibits the current generated by the Kv4.3 channels to that of the Kv4.3 channels in the presence of DREAM. FIG. 1A shows a representative example of the effects of (35) (100 nM) on Kv4.3 or Kv4.3+DREAM channels. Graph B of FIG. 1 shows a bar chart comparing the inhibitory effect of the Kv4.3 and Kv4.3+DREAM current produced by (35), (42) and (62) at 100 nM.

Example 3: Neuroprotective Effect of the Compounds of the Invention on Q111DR Cells In an immortalized cell line of mouse striatum infected with lentivirus STHdh$^{Q111/Q111}$ expressing the complete human DREAM protein (Q111DR), the neuroprotective effect of the compounds was tested against necrosis mediated by H$_2$O$_2$ and apoptosis mediated by staurosporine.

Figure 2:
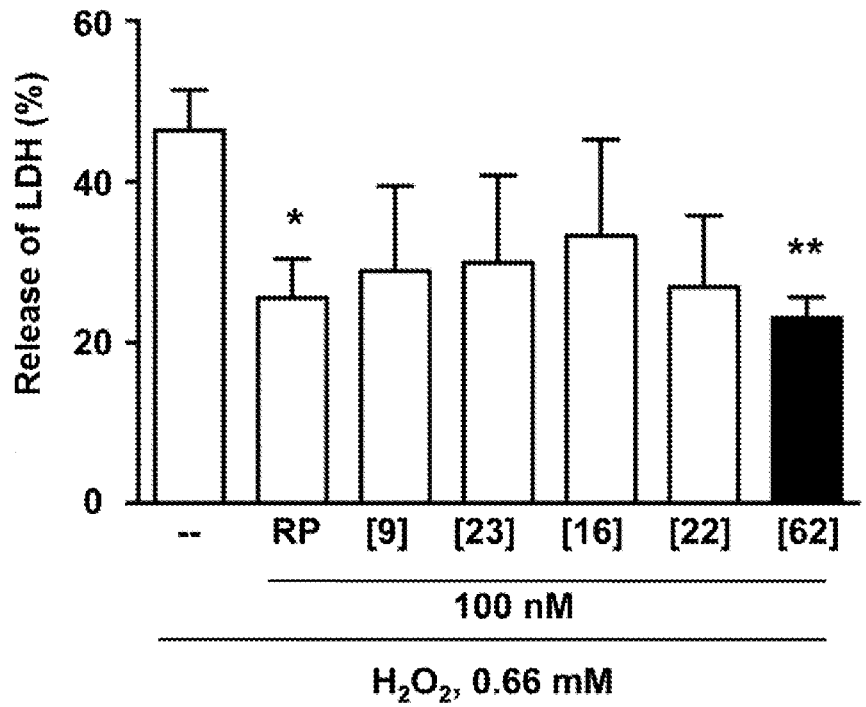
FIG. 2. Shows the analysis of the neuroprotective effect shown by compounds 9, 16, 22, 23 and 62 (100 nM) against the rupture the cell membrane mediated by $H_2O_2$ (0.66 mM) and subsequent release of LDH (lactate dehydrogenase) in STHdh$^{Q111/Q111}$ cells infected with lentivirus expressing the complete human DREAM protein. RP: Repaniglida.

FIG. 2 shows a representative example of the ability of the compounds to inhibit the release of the lactate dehydrogenase enzyme, which is a reflection of their inhibitory effect of cell death caused by oxidative stress in response to exposure to H$_2$O$_2$. It is clearly the lowest LDH release and therefore the neuroprotective effect of compound (62).

Figure 3:
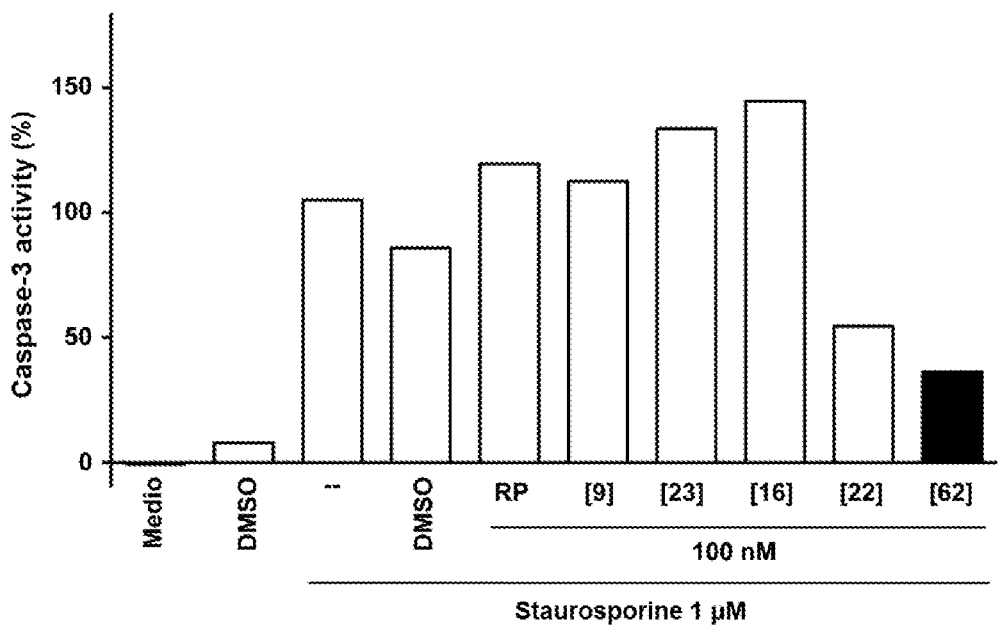
FIG. 3. Analysis of the neuroprotective effect of compounds 9, 16, 22, 23 and 62 (100 nM) against the activation of caspase-3 mediated by staurosporine in $^{Q111/Q111}$ cells infected with lentivirus expressing the complete human DREAM protein. The caspase-3 activity was measured after 1 h of pre-incubation of the compounds (100 nM) and subsequent exposure for 5 h of staurosporine at 1 μM. RP: Repaniglida.

FIG. 3 shows a representative example of the effect of the compounds on the activation of caspase-3 associated with induced cell death due to treatment with staurosporine. It is clearly the lowest activation of caspase-3 and therefore the inhibition of apoptosis and the neuroprotective effect of compound (62) compared with repaglinide (RP), a previously described neuroprotective agent.

The invention claimed is:
1. A compound selected from the group consisting of:
2-[2-(3,4-dichlorophenyl)acetylamino]-4-methoxybenzoic acid,
4-chloro-2-[2-(3-phenoxyphenyl)acetylamino]benzoic acid,
4-chloro-2-[2-(4-chloro-2-fluorophenyl)acetylamino] benzoic acid,
4-chloro-2-[2-(3,4-dichlorophenyl)acetylamino]methyl benzoate,
4-chloro-2-[2-(3,4-dihydroxyphenyl)acetylamino]benzoic acid,
4-chloro-2-[3-(3,4-dichlorophenyl)propanoylamino] benzoic acid,
4-chloro-2-[2-(3,4-dichlorophenyl)acetylamino]-N-methylbenzamide,
3-[2-(3-phenoxyphenyl)acetylamino]-2-naphthoic acid,
3-[3-(3,4-dichlorophenyl)propanoylamino]-2-naphthoic acid,
4-bromo-2-[2-(3,4-diclorophenyl)acetylamino]benzoic acid,
2-[2-(3,4-dichlorophenyl)acetylamino]-5-(4'-n-butylphenyl)benzoic acid,
2-[2-(3,4-dichlorophenyl)acetylamino]-4-(4'-n-butylphenyl)benzoic acid,
2-[2-(3,4-dichlorophenyl)acetylamino]-5-(4'-tert-butylphenyl)benzoic acid,
2-[2-(3,4-dichlorophenyl)acetylamino]-5-(2'-methylphenyl)benzoic acid,
2-[3-(3,4-dichlorophenyl)propanoylamino]-5-(4'-n-butylphenyl)benzoic acid,
2-[2-(3,4-dichlorophenyl)acetylamino]-4-phenylbenzoic acid,
2-[2-(3,4-dichlorophenyl)acetylamino]-4-(2'-methylphenyl)benzoic acid,
2-[3-(3,4-dichlorophenyl)propanoylamino]-4-phenylbenzoic acid,
2-[2-(3,4-dichlorophenyl)acetylamino]-5-phenylbenzoic acid,
2-[3-(3,4-dichlorophenyl)propanoylamino]-5-(4'-tert-butylphenyl)benzoic acid,
2-[3-(3,4-dichlorophenyl)propanoylamino]-5-(2'-methylphenyl)benzoic acid,
2-[3-(3,4-dichlorophenyl)propanoylamino]-4-(2'-methylphenyl)benzoic acid,
2-[2-(3,4-dichlorophenyl)acetylamino]-4-ethynylbenzoic acid,
2-[2-(3,4-dichlorophenyl)acetylamino]-methyl 5-phenylbenzoate,
2-[2-(3,4-dichlorophenyl)acetylamino]-5-(2'-methylphenyl)methyl benzoate,

2-[2-(3,4-dichlorophenyl)acetylamino]-5-(4'-tert-butylphenyl)methyl benzoate,
2-[2-(3,4-dichlorophenyl)acetylamino]-5-(4'-n-butylphenyl)methyl benzoate,
2-[2-(3,4-dichlorophenyl)acetylamino]-methyl 4-phenylbenzoate,
2-[2-(3,4-dichlorophenyl)acetylamino]-4-(2'-methylphenyl)methyl benzoate,
2-[2-(3,4-dichlorophenyl)acetylamino]-4-(4'-n-butylphenyl)methyl benzoate,
2-[3-(3,4-dichlorophenyl)propanoylamino]-methyl 5-phenylbenzoate,
2-[3-(3,4-dichlorophenyl)propanoylamino]-5-(2'-methylphenyl)methyl benzoate,
2-[3-(3,4-dichlorophenyl)propanoylamino]-5-(4'-n-butylphenyl)methyl benzoate,
2-[3-(3,4-dichlorophenyl)propanoylamino]-methyl 4-phenylbenzoate,
2-[3-(3,4-dichlorophenyl)propanoylamino]-4-(2'-methylphenyl)methyl benzoate,
2-[3-(3,4-dichlorophenyl)propanoylamino]-4-(4'-n-butyl phenyl)methyl benzoate,
2-[3-(3,4-dichlorophenyl)propanoylamino]-5-phenylbenzoic acid,
N-(2-benzoylphenyl)-2-(3,4-dichlorophenyl)acetamide and
2-[3-(3,4-dichlorophenyl)propanoylamino]-4-(4'-n-butylphenyl)benzoic acid.

2. A compound of the formula (2R)-2-[2-(3,4-dichlorophenyl)acetylamino]-3-(1-trityl-1H-imidazol-4-yl)methyl propanoate.

3. A pharmaceutical composition comprising the compound of claim 2.

4. A pharmaceutical composition comprising the compound of claim 1.

5. A method for treating a disease or disorder in which the DREAM protein has altered expression levels comprising administering to a person in need thereof the pharmaceutical composition according to claim 4 and wherein the disease or disorder in which expression levels of the DREAM protein are altered is selected from neurodegenerative disorders, cognitive disorders, sensory perception disorders, inflammatory response disorders and auto inflammatory diseases.

6. The method according to claim 5 wherein the disease or disorder in which expression levels of the DREAM protein are altered is selected from Alzheimer's disease and other types of dementia, schizophrenia, Huntington's disease, dyskinesia, depression, Down's syndrome, chronic pain, neuropathic pain, allodynia, atherosclerosis, type-2 diabetes, rheumatoid arthritis, gout or acute respiratory distress syndrome.

* * * * *